(12) United States Patent
Babic et al.

(10) Patent No.: US 10,190,988 B2
(45) Date of Patent: Jan. 29, 2019

(54) METHODS OF LASER WELDING DISPOSABLE DIAGNOSTIC TEST ELEMENTS

(71) Applicant: Roche Diabetes Care, Inc., Indianapolis, IN (US)

(72) Inventors: Branislav Babic, Ludwigshafen (DE); Carina Horn, Biblis (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 117 days.

(21) Appl. No.: 15/086,308

(22) Filed: Mar. 31, 2016

(65) Prior Publication Data

US 2016/0209331 A1    Jul. 21, 2016

Related U.S. Application Data

(63) Continuation of application No. PCT/EP2014/075429, filed on Nov. 24, 2014.

(30) Foreign Application Priority Data

Nov. 27, 2013 (EP) .................................... 13194706

(51) Int. Cl.
*G01N 21/75* (2006.01)
*G01N 21/77* (2006.01)
(Continued)

(52) U.S. Cl.
CPC ........ *G01N 21/77* (2013.01); *B01L 3/502707* (2013.01); *B23K 26/0006* (2013.01);
(Continued)

(58) Field of Classification Search
CPC .......... B29C 66/8322; B29C 66/73343; B29C 66/24; B29C 66/71; B29C 66/73921;
(Continued)

(56) References Cited

U.S. PATENT DOCUMENTS

| 4,776,904 A | 10/1988 | Charlton et al. |
| 2007/0278097 A1 | 12/2007 | Bhullar et al. |

FOREIGN PATENT DOCUMENTS

| EP | 1864784 A1 | 12/2007 |
| JP | 2001026656 | 1/2001 |

(Continued)

OTHER PUBLICATIONS

Japanese Office Action, English Translation-in-Part, dated Oct. 16, 2018.

*Primary Examiner* — Dennis White

(57) ABSTRACT

Methods are provided for manufacturing disposable diagnostic test elements via laser welding, where the methods include providing, in a stacked or layered arrangement, a base layer, a cover layer, and optionally an intermediate layer, where one of the layers is an absorbing layer and at least one other of the layers is a transparent layer, and where one of the layers includes a coating adapted to interact with a body fluid sample when conducting a test on the resulting test element; directing a laser beam in a weld area through the at least one transparent layer and against the absorbing layer; and fusing the transparent and the absorbing layers together to form the test element, where the coating covers the weld area at least in part and absorbs and/or scatters radiation from the laser beam at least in part. Disposable diagnostic test elements also are provided.

20 Claims, 3 Drawing Sheets

(51) Int. Cl.
  *B23K 26/57*   (2014.01)
  *B01L 3/00*    (2006.01)
  *B29C 65/16*   (2006.01)
  *B29C 65/00*   (2006.01)
  *B23K 26/00*   (2014.01)
  *G01N 33/50*   (2006.01)
  *B23K 103/00*  (2006.01)
  *B29L 31/00*   (2006.01)

(52) U.S. Cl.
  CPC .......... *B23K 26/57* (2015.10); *B29C 65/1635* (2013.01); *B29C 65/1683* (2013.01); *B29C 66/112* (2013.01); *B29C 66/1122* (2013.01); *B29C 66/131* (2013.01); *B29C 66/24* (2013.01); *B29C 66/53461* (2013.01); *B29C 66/723* (2013.01); *B29C 66/73343* (2013.01); *B29C 66/73365* (2013.01); *B29C 66/81267* (2013.01); *B29C 66/8242* (2013.01); *B29C 66/8322* (2013.01); *G01N 33/50* (2013.01); *B01L 2300/044* (2013.01); *B01L 2300/0816* (2013.01); *B01L 2300/0887* (2013.01); *B01L 2400/0406* (2013.01); *B23K 2103/42* (2018.08); *B23K 2103/50* (2018.08); *B29C 65/1654* (2013.01); *B29C 65/1677* (2013.01); *B29C 66/71* (2013.01); *B29C 66/73921* (2013.01); *B29K 2995/0027* (2013.01); *B29L 2031/756* (2013.01); *G01N 2021/7769* (2013.01)

(58) Field of Classification Search
  CPC ............ B29C 65/1677; B29C 65/1654; B29C 66/723; B29C 66/1122; B29C 65/1635; B29C 65/1683; B29C 66/112; B29C 66/131; B29C 66/53461; B29C 66/73365; B29C 66/81267; B29C 66/8242; B23K 2203/50; B23K 2203/42; B23K 26/0063; B23K 26/0006; G01N 2021/7769; G01N 21/77; G01N 33/50; B29K 2995/0027; B01L 2300/0887; B01L 2300/044; B01L 2400/0406; B01L 2300/0816; B01L 3/502707; B29L 2031/756
  See application file for complete search history.

(56) References Cited

FOREIGN PATENT DOCUMENTS

| | | |
|---|---|---|
| JP | 2005074796 | 11/2006 |
| JP | 2006310828 | 11/2006 |
| JP | 2008156432 | 3/2016 |

METHODS OF LASER WELDING DISPOSABLE DIAGNOSTIC TEST ELEMENTS

CROSS-REFERENCE TO RELATED APPLICATIONS

This patent application is a continuation of Int'l Patent Application No. PCT/EP2014/075429 (filed 24 Nov. 2014), which claims priority to and the benefit of EP Patent Application No. 13194706.1 (filed 27 Nov. 2013). Each patent application is incorporated herein by reference as if set forth in its entirety.

TECHNICAL FIELD

This disclosure relates generally to engineering and medical diagnostics, and more particularly, it relates to methods of manufacturing disposable diagnostic test elements via laser welding and also relates to test elements manufactured by such methods.

BACKGROUND

In designs of diagnostic test elements, it is known to combine several layers by means of double-sided adhesive tapes, which allows processing from roll-to-roll of web materials thus achieving a high output and yield in the manufacturing process. However, using adhesive tapes contributes to production costs and often requires specific adhesive compounds adapted to the chemistry of the test.

It also is known to fabricate multilayer biosensors by means of laser welding, where a laser-transparent material is fused on a laser-absorbing material. The latter is melted by the laser energy and connected to the transparent material. To date, such techniques were limited to clean "black" and "clear" layer configurations.

For the foregoing reasons, there is a need for improved methods of manufacturing disposable diagnostic test elements.

BRIEF SUMMARY

An inventive concept described herein includes processing coated assemblies via laser welding to manufacture disposable diagnostic test elements that allow specific sample interaction in a specific test format. This inventive concept is achieved by providing at layered structure for the test elements during manufacture, where at least one layer is an absorbing layer and at least one other of the layers is a transparent layer, and where a coating is provided to one of the layers and covers a weld area at least in part and absorbs and/or scatters laser radiation at least in part. This inventive concept can be incorporated into exemplary methods and devices as described herein and in more detail below.

For example, methods are provided for manufacturing disposable diagnostic test elements via laser welding. Such methods can include a step of providing, in a stacked or a layered arrangement, a base layer, a cover layer, and optionally an intermediate layer, where one of the layers is an absorbing layer configured to absorb radiation from a laser beam and at least one of the other layers is a transparent layer permeable for the laser radiation, and where one of the layers includes a coating adapted to interact with a body fluid sample when conducting a test with a resulting test element.

In addition, the methods can include a step of directing the laser beam in a weld area through the at least one transparent layer and against the absorbing layer to fuse the transparent and the absorbing layers together to form the test elements. In some instances, the base layer and the cover layer can be fused together in a one-dimensional (1-D) connection along a continuous line or an intermittent line. To strengthen the resulting weld, this step also can include simultaneous pressing the layers to form a composite member. In other instances, the weld area is formed as a weld seam that seals a zone of the test elements.

In the methods, the coating is a chemistry layer adapted to react with an analyte of interest in the body fluid sample when conducting the test with the resulting test element, and where the coating covers the weld area at least in part and absorbs and/or scatters the laser radiation at least in part. In some instances, especially when the test elements are intended for optical measurement, the coating includes one or more light-scattering particles such as $TiO_2$, $BaTiO_3$, $ZrO_2$, $ZrSiO_3$ and $BaSO_4$. Additionally or alternatively, the coating can include one or more of an organic polymer, a pigment, and a mineral filler. Additionally or alternatively, the coating can include one or more components that melt upon impact of the radiation from the laser beam.

To improve fluidic interaction with the body fluid sample during a test, the coating can be further adapted to increase the wettability of the coated layer when wetted with the body fluid sample. In this manner, the coating can include a detergent and/or a hydrophilic component.

Likewise, the methods can include a step of positioning the coating as a chemistry layer on a foil blank to form the intermediate layer, and then laser welding the intermediate layer between the base layer and the cover layer. In this manner, the base layer and the cover layer can be cut as blanks from a foil material, where one foil material is generally laser beam absorbent and the other foil material is generally laser beam transparent.

Moreover, the methods can include a step of forming a capillary channel configured to transport the body fluid sample in the base layer and/or the cover layer, and arranging the coating at least in part in the area of the capillary channel.

Furthermore, the methods can include a step of transporting from roll-to-roll continuous webs as feed material, the base and cover layers, and then laser welding the continuous webs to form a plurality of test elements.

In some instances, the methods also can include a step of molding the base layer and the cover layer as three-dimensional (3D)-formed parts from a plastic material, where the fusing can include simultaneous pressing of the base layer, the cover layer and the optional intermediate layer to form a composite member.

The resulting disposable diagnostic test elements can be formed as test strips that can be manually handled or as a test tape that can be wound on a spool (e.g., in a test tape cassette).

In view of the foregoing methods, disposable diagnostic test elements also are provided, where such test elements are manufactured according to the methods disclosed herein.

On this basis, an object of this disclosure is to improve known methods and products to achieve an improved material and production efficiency and a reliable test architecture.

Advantageously, laser welding obviates a need for adhesives and adhesive tapes, thereby reducing material expenditure and avoiding additional process steps. Surprisingly, it has been found that coated structures, which absorb and/or scatter at least a part of the radiation from a laser beam, do not impede or weaken the resulting connection with regard to weld strength and sealing ability. Breaking down a prejudice among experts, it has been found that such laser-responsive interfaces even contribute to forming an adherent composite. Moreover, specific interaction with a body fluid sample can be integrated in the test architecture.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
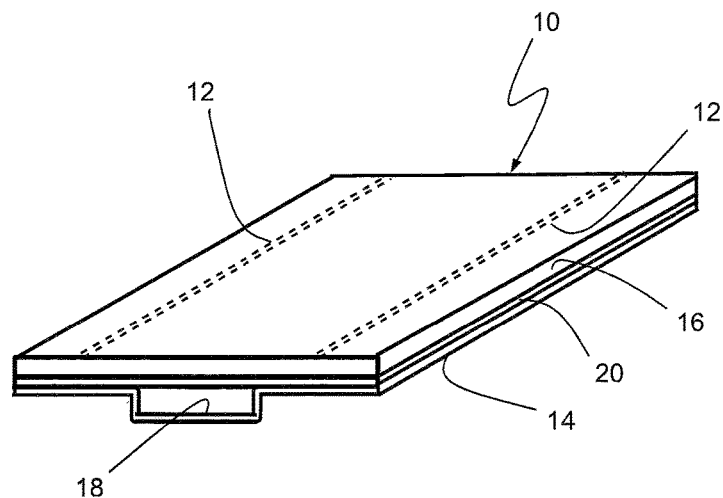
FIG. 1 is a perspective view of an exemplary embodiment of a test element or capillary test strip having sheet materials fused by laser welding.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods and devices now will be described more fully hereinafter with reference to the accompanying drawings, in which some, but not all embodiments of the inventive concept are shown. Indeed, the methods and devices may be embodied in many different forms and should not be construed as limited to the embodiments set forth herein; rather, these embodiments are provided so that this disclosure will satisfy applicable legal requirements.

Likewise, many modifications and other embodiments of the methods and devices described herein will come to mind to one of skill in the art to which the disclosure pertains having the benefit of the teachings presented in the foregoing descriptions and the associated drawings. Therefore, it is to be understood that the methods and devices are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods and devices, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Methods of manufacturing disposable diagnostic test elements are described in further detail below. The methods are based on an inventive concept that includes processing coated assemblies for allowing specific sample interaction in a specific test format. Correspondingly it is proposed herein to provide in an initial step one of the layers forming test elements with a coating in the form of a dry chemistry layer adapted to react with an analyte in a body fluid sample when conducting a test, where the coating covers a weld area at least in part and absorbs and/or scatters radiation from a laser beam at least in part. It shall be understood that this disclosure relates to the disposable test elements produced by such methods.

Methods of Manufacturing Disposable Diagnostic Test Elements and the Resulting Test Elements Referring to the drawings, a composite test element 10 is shown as a disposable for a diagnostic test that can be prepared by fusing multiple layers or elements along one or more laser weld lines 12, thereby avoiding a need for adhesive components.

In the exemplary embodiment illustrated in FIG. 1, a composite test element 10 includes a fusible, base layer 14 that can absorb radiation from a laser beam, as well as a fusible, transparent cover layer 16 that is permeable to radiation from the laser beam. The base layer 14 includes an absorptive (or black) foil blank with a deep-drawn capillary channel 18, which can be loaded with a body fluid sample (e.g. for a blood glucose test). On the side facing the capillary channel 18, the flat cover layer 16 can be provided with a coating 20 that is adapted to interact with the body fluid sample when conducting a diagnostic test.

The coating 20 may be configured to promote wettability or hydrophilic properties of the coated area, such as to promote transport or distribution of the body fluid sample. For example, the cover layer 16 may be formed from a transparent polycarbonate foil of, for example, about 140 μm thickness, and the coating 20 may include polar coating agents such as hydroxyethyl cellulose (e.g., available from SE Tylose GmBH & Co. KG under the trademark Tylose®) and colloidal silica (e.g., available from Akzo Nobel N. V. under trademark Bindzil®).

As the coating 20 is applied across the entire interface side of the cover layer 16, it also overlaps one or more weld areas (i.e. the lines) 12, where a laser beam passes during laser welding. In this manner, the laser beam is directed through the transparent cover layer 16 and its coating 20 against the base layer 14, where the dark, absorptive material absorbs laser energy and melts to bond to the adjacent cover layer 16. As the weld areas 12 border and seal the capillary channel 18 on both sides, body fluid is prevented from bypassing a transport zone. At the same time, the body fluid receiving area is shielded against environmental influence.

Although the cover layer 16 is transmissive for radiation from the laser beam, the coating 20 also can include components that absorb and/or scatter laser radiation at least in part. These components also may melt upon impact of the laser beam. Surprisingly, it has been found that such shading or scattering does not affect the strength and seal of the weld areas 12. In this context, it should be understood that the weld areas 12 are arranged at a distance from the edges of the composite test element 10, and the laser beam energy is adjusted for proper welding, but not for cutting at the same time.

Figure 2:
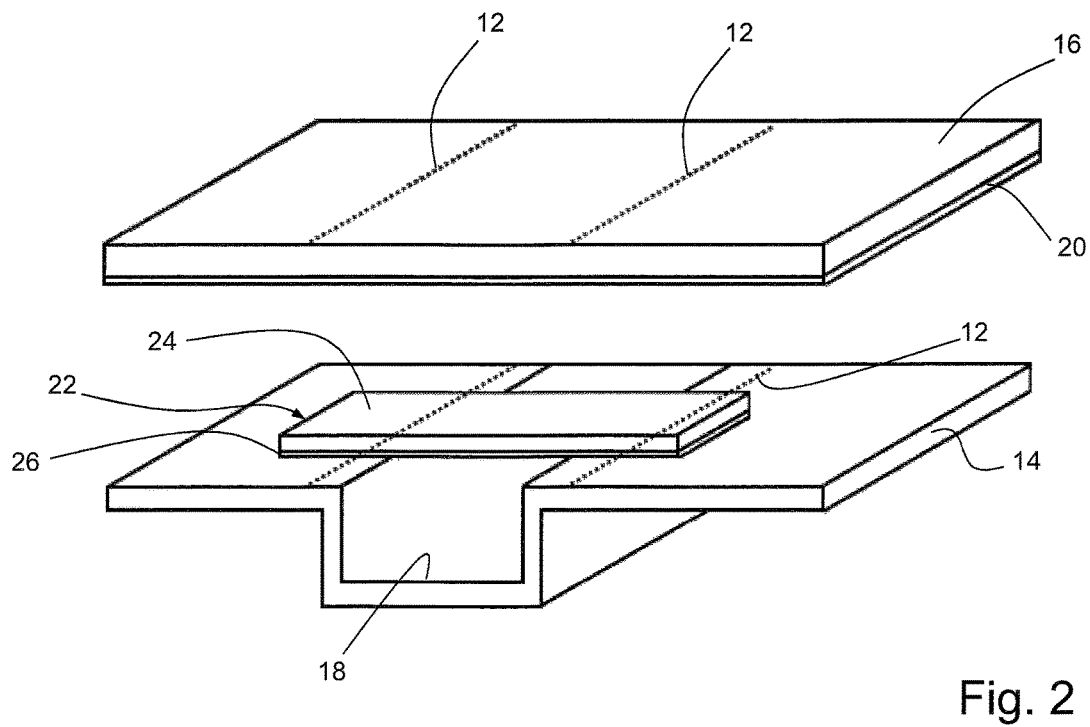
FIG. 2 is an exploded, perspective view illustrating an alternative embodiment that includes an intermediate layer of fusible material.

In an exemplary embodiment illustrated in FIG. 2, the same or similar parts have been provided with the same reference numerals as previously described. This embodiment differs in that an intermediate reagent layer 22 is interposed between the base layer 14 and the cover layer 16.

The reagent layer 22 includes a transparent foil blank or carrier 24 and a dry chemistry layer 26 deposited on the carrier 24 and overlapping a part of the capillary channel 18. The chemistry layer 26 is adapted to irreversibly react with an analyte of interest (e.g., glucose) in the body fluid sample, such that a product of the reaction can be detected by, for example, a reflection-photometric device. For this purpose, the chemistry layer 26 includes one or more organic polymers, pigments, and mineral fillers. The pigments effect an increase in the strength of the measurement signal and may be selected from $TiO_2$, $BaTiO_3$, $ZrO_2$, $ZrSiO_3$ and/or $BaSO_4$. It is also envisioned that fine-grained particles can be incorporated in the chemistry layer 26, which have a strong light-scattering effect due to a high refractive index of at least about 2.5.

The stack of layers 14, 16, 22 is subjected to pressing and simultaneous welding action along weld areas 12, where the laser beam is directed through the cover layer 14 and the intermediate layer 22 onto the fusible base layer 14. Again, and surprisingly, it has been found that such layered compositions of an intermediate layer 22 do not significantly weaken the resulting laser welds at weld areas 12.

Figure 3:
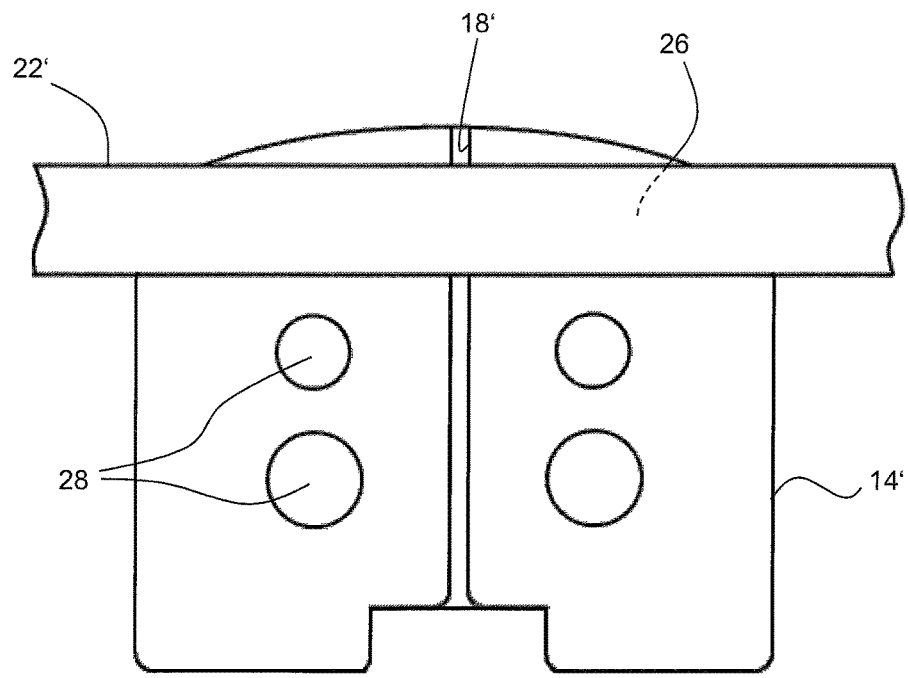
FIG. 3 shows a top view of a portion of another alternate embodiment that includes a molded base layer and a reagent strip.
Figure 4:
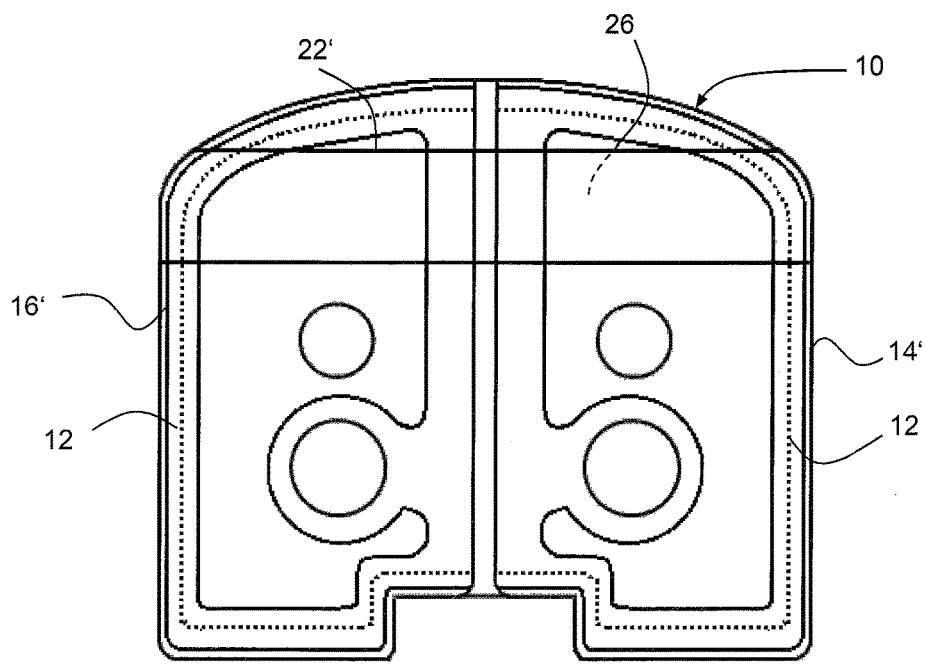
FIG. 4 shows an assembled embodiment of FIG. 3 including a laser-fused cover layer.

FIGS. 3 and 4 illustrate another exemplary embodiment of a composite test element 10 for a single-use diagnostic test. In this embodiment, the laser welded members are molded 3-D plastic layers 14', 16' in combination with an intermediate reagent strip layer 22'. The test element 10 is intended for a one-step test, where an integrated needle (not shown) is used in a reciprocating movement to pierce the skin of a user and to apply sampled blood onto the test strip layer 22'.

As best seen from FIG. 3, the base layer 14 has a capillary channel 18' provided to guide an inserted sampling needle. Further, hole structures 28 allow form-fitting connection to a measuring device, which also has a drive to engage the needle. The base layer 14' is absorptive with respect to laser radiation used for welding. Furthermore, the reagent test strip layer 22' includes a chemistry layer or coating 26 facing the capillary channel 18' and being adapted to react with an analyte of interest in the body fluid, where the coating 26 absorbs and/or scatters the laser radiation at least in part.

FIG. 4 shows the assembled composite test element 10 including a transparent cover layer 16' that is fused to the base layer 14' by laser welding along peripheral weld lines 12. As in the embodiments exemplified above, the coating 26 covers the weld lines 12 at least in part and hence takes up a fraction of the laser energy. Albeit it has been proven that the laser-welded layers 14', 16' can be firmly connected to such an extent that a manual disassembly is not possible.

Figure 5:
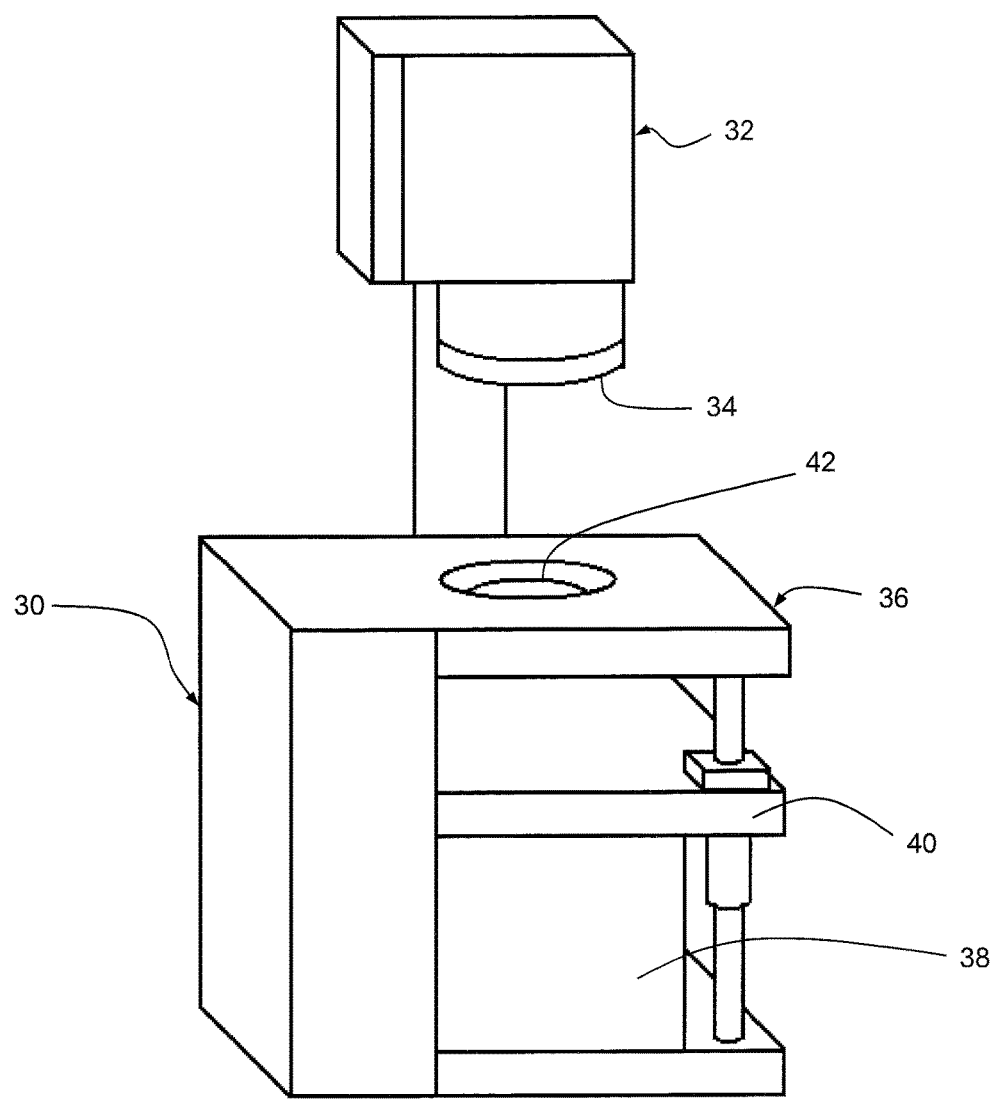
FIG. 5 is a diagrammatic view of a laser welding system for producing composite test elements.

FIG. 5 illustrates a laser welding system 30 useful in forming the composite test elements 10 described herein. The system 30 includes a laser apparatus 32 including optics 34, a clamping unit 36 for the components to be welded, and a hydraulic actuator 38 to actuate the clamping unit 36. The latter includes a carrier plate 40 to position the layers 14, 16, 22 in a stacked manner and a transparent counter plate 42. The carrier plate 40 can be moved upwards by means of the hydraulic actuator 38, such that pressure is put on the composite layers during activation of the laser apparatus 32. In the welding process, the coating layers 20, 26 melt upon laser impact and are fused together with the base and cover layers 14, 16.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS 10 composite test element
12 laser weld area(s)/laser weld line(s)
14/14' base layer
16/16' cover layer
18/18' capillary channel
20 coating
22/22' reagent layer
24 foil blank or carrier
26 coating/dry chemistry layer
28 hole structures
30 laser welding system
32 laser apparatus
34 optics
36 clamping unit
38 hydraulic actuator
40 carrier plate
42 counter plate

The invention claimed is:
1. A method of manufacturing a disposable diagnostic test element, the method comprising the steps of:

a) providing, in a stacked or a layered arrangement, a base layer, a cover layer, and optionally an intermediate layer, wherein one of the layers is an absorbing layer configured to absorb radiation from a laser beam and at least one of the other layers is a transparent layer configured to transmit radiation from the laser beam, and wherein one of the layers includes a coating adapted to interact with a body fluid sample when conducting a test with a resulting test element;

b) directing the laser beam in one or more weld areas through the at least one transparent layer and against the absorbing layer; and c) fusing the transparent and the absorbing layers together by radiation from the laser beam to form the test element, wherein the coating is a chemistry layer adapted to react with an analyte of interest in the body fluid sample when conducting the test with the resulting test element, and wherein the coating covers the weld area and absorbs and/or scatters the laser radiation at least in part.

2. The method of claim 1, wherein the coating comprises one or more components that melt upon impact by the laser beam.

3. The method of claim 1, wherein the coating comprises one or more components that increase wettability of the coated layer when wetted with the body fluid sample.

4. The method of claim 3, wherein the one or more components that increase wettability of the coated layer are a detergent and/or a hydrophilic component.

5. The method of claim 1, wherein the coating comprises one or more light-scattering particles selected from the group consisting of $TiO_2$, $BaTiO_3$, $ZrO_2$, $ZrSiO_3$ and $BaSO_4$.

6. The method claim 1, wherein the coating comprises at least one of an organic polymer, a pigment, and a mineral filler.

7. The method of claim 1, further comprising the step of: depositing the coating as a chemistry layer on a foil blank to form the intermediate layer and laser welding the intermediate layer between the base layer and the cover layer.

8. The method of claim 1, further comprising the steps of: forming a capillary channel configured to transport the body fluid sample in the base layer and/or the cover layer; and arranging the coating at least in part in the area of the capillary channel.

9. The method of claim 1, wherein the base layer and the cover layer are fused together along a continuous line or an intermittent line.

10. The method of claim 1, wherein the weld area is formed as a weld seam that seals a zone of the test element configured to receive the body fluid sample.

11. The method of claim 1, further comprising the step of: cutting the base and cover layers from a foil material.

12. The method of claim 1, further comprising the steps of:
transporting from roll-to-roll continuous webs as feed material for the base and cover layers; and
laser welding the continuous webs to form a plurality of test elements.

13. The method of claim 1, wherein the test element is formed as a test strip that can be manually handled or as a test tape that can be wound on a spool.

14. The method of claim 1, wherein the base layer and the cover layer are cut from a foil material that is laser beam-absorbent or laser beam-transmissible.

15. The method of claim 1, further comprising the step of: molding the base layer and the cover layer as three-dimensional-formed parts from a plastic material.

16. The method of claim 1, wherein the fusing step includes simultaneous pressing the base layer, the cover layer, and the optional intermediate layer to form a composite member.

17. A disposable diagnostic test element for analyzing a body fluid sample having or suspected of having an analyte of interest, the test element comprising:
a stacked or layered arrangement of a base layer, a cover layer, and optionally an intermediate layer, wherein one of the layers is made of an absorbing material configured to absorb radiation from a laser beam and at least one other of the layers is made of a transparent material configured to transmit radiation from the laser beam, wherein the absorbing and transparent materials are fused together in a weld area by laser welding seams, wherein at least one of the layers includes a coating in the form of a chemistry layer adapted to react with the analyte of interest when conducting a test, and wherein the coating covers the weld area and contains one or more components that absorb and/or scatter the radiation from the laser beam at least in part.

18. The disposable diagnostic test element of claim 17, wherein the coating comprises one or more components that increase wettability of the coated layer when wetted with the body fluid sample.

19. The disposable diagnostic test element of claim 18, wherein the one or more components that increase wettability of the coated layer are a detergent and/or a hydrophilic component.

20. The disposable diagnostic test element of claim 17, wherein the coating comprises one or more light-scattering particles selected from the group consisting of $TiO_2$, $BaTiO_3$, $ZrO_2$, $ZrSiO_3$ and $BaSO_4$.

* * * * *